United States Patent
Lloyd et al.

(10) Patent No.: US 9,364,345 B2
(45) Date of Patent: Jun. 14, 2016

(54) SURGICAL IMPACTOR

(75) Inventors: Russell Lloyd, Swindon (GB); Mona Alinejad, London (GB); David Wycliffe Murray, Oxford (GB); Christopher Dodd, Oxford (GB); Paul James Kistle, Wroughton (GB); Nigel John Bird, Grange Park (GB)

(73) Assignee: BIOMET UK LIMITED (GB)

( * ) Notice: Subject to any disclaimer, the term of this patent is extended or adjusted under 35 U.S.C. 154(b) by 60 days.

(21) Appl. No.: 13/379,934

(22) PCT Filed: Jul. 1, 2010

(86) PCT No.: PCT/GB2010/001275
§ 371 (c)(1),
(2), (4) Date: Mar. 12, 2012

(87) PCT Pub. No.: WO2011/001150
PCT Pub. Date: Jan. 6, 2011

(65) Prior Publication Data
US 2012/0184966 A1    Jul. 19, 2012

(30) Foreign Application Priority Data
Jul. 1, 2009   (GB) .................................. 0911432.3

(51) Int. Cl.
*A61F 2/46*    (2006.01)
*A61F 2/38*    (2006.01)

(52) U.S. Cl.
CPC ................ *A61F 2/461* (2013.01); *A61F 2/389* (2013.01); *A61F 2002/4627* (2013.01)

(58) Field of Classification Search
CPC ........................................... A61B 2017/00353
USPC ........... 623/13.12, 20.14, 20; 606/99, 88, 277
See application file for complete search history.

(56) References Cited

U.S. PATENT DOCUMENTS 4,459,985 A    7/1984   McKay et al.
4,781,182 A *  11/1988  Purnell et al. ................... 606/96

(Continued)

FOREIGN PATENT DOCUMENTS

CA    2568885 A1    5/2008
JP    2003-513706 A  4/2003

(Continued)

OTHER PUBLICATIONS

Great Britain Search Report mailed Oct. 19, 2009 for GB0911432.3 of which PCT/GB2010/001275, filed Jul. 1, 2010 claims benefit; of which U.S. Appl. No. 13/379,934 filed Mar. 12, 2012 claims benefit.

(Continued)

*Primary Examiner* — Samuel Hanna
(74) *Attorney, Agent, or Firm* — Schwegman Lundberg & Woessner, P.A.

(57) ABSTRACT

A surgical impactor (2) for inserting a prosthetic implant (26) into a bone, the surgical impactor (2) comprising: a movable retaining means (8) for releasably connecting the implant (26) to the surgical impactor (2), wherein the movable retaining means (8) has a first position in which the implant (26) is connected to the surgical impactor (2) and a second position in which the implant (26) is not connected to the surgical impactor (2); and a mechanism (14, 16) for moving the movable retaining means (8) between the first and second positions, wherein the movable retaining means (8) and the mechanism (14, 16) are removable from the surgical impactor (2).

11 Claims, 3 Drawing Sheets

(56) References Cited

U.S. PATENT DOCUMENTS

| | | |
|---|---|---|
| 5,030,221 A | 7/1991 | Buechel et al. |
| 6,063,124 A | 5/2000 | Amstutz |
| 6,520,966 B1 | 2/2003 | Kohler et al. |
| 6,743,258 B1 | 6/2004 | Keller |
| 2004/0162619 A1 | 8/2004 | Blaylock et al. |
| 2005/0033306 A1 | 2/2005 | Keller |
| 2007/0239168 A1* | 10/2007 | Kuenzi et al. ............... 606/96 |
| 2009/0036909 A1 | 2/2009 | Perry et al. |
| 2010/0010490 A1* | 1/2010 | Brigido ............ A61B 17/1725 606/64 |

FOREIGN PATENT DOCUMENTS

| | | |
|---|---|---|
| JP | 2005536281 A | 12/2005 |
| JP | 2006-524532 A | 11/2006 |
| WO | WO-2011001150 A1 | 1/2011 |

OTHER PUBLICATIONS

Japanese Office Action mailed Apr. 18, 2014 for JP Application No. 2012-519047.

Australian Patent Examination Report No. 2 for Australian patent application No. 2010267756 issued Jul. 4, 2014.

"International Application Serial No. PCT/GB2010/001275, International Preliminary Report on Patentability mailed Jan. 12, 2012", 6 pgs.

"International Application Serial No. PCT/GB2010/001275, International Search Report mailed Nov. 19, 2010", 4 pgs.

"International Application Serial No. PCT/GB2010/001275, Written Opinion mailed Nov. 19, 2010", 4 pgs.

* cited by examiner

SURGICAL IMPACTOR

CROSSS REFERENCE TO RELATED APPLICATIONS

This application is a 371 U.S. National Stage of International Application No. PCT/GB2010/001275, filed Jul. 1, 2010. This application claims priority to United Kingdom Patent Application No. GB0911432.3, filed Jul. 1, 2009. The disclosures of the above applications are incorporated herein by reference.

This invention relates to a surgical impactor for inserting a prosthetic implant into a bone, and particularly but not exclusively relates to a surgical impactor for inserting a cementless tibial implant as part of a partial knee replacement.

BACKGROUND

Bearing surfaces of joints may become worn or damaged by arthritis over time. Where this occurs, it is common to replace the damaged surface with an artificial surface in the form of a prosthetic.

In a knee replacement, the bearing surfaces are replaced by a prosthetic which comprises a femoral implant and a tibial implant (tibial tray), which interface through a bearing disposed between the two implants.

A unicompartmental or partial knee replacement may be carried out where only one of the medial or lateral compartments is damaged. This helps to conserve undamaged bone and restores more natural movement. Also, due to the small size of the prosthetic, the surgery may be less invasive than a total knee replacement.

Following resection of the joint surfaces to remove the damaged bone, the prosthetic implants are secured to the resected bone. For the tibial implant, a slot is cut into the tibial plateau to receive a keel which protrudes from a bottom surface of the tibial implant.

The keel of the tibial implant may be secured in the slot by a self curing polymer compound known as bone cement. However, the bone cement may degrade over time and crack. As an alternative, the slot may be sized so that the keel and slot have an interference fit. In this case, no cement is require and the implant is secured solely by the interference fit. This method of fixation is commonly known as 'cementless'.

Where a cementless implant is used, it is necessary to force the keel into the slot. Due to the size of the operative wound, particularly in a unicompartmental or partial knee replacement, it is difficult for the surgeon to provide the necessary force in order to force the keel into the slot. To aid the surgeon, a tibial impactor may be used. A tibial impactor has an impaction member which is inserted into the operative wound and a extension arm which is connected to the impaction member but extends out of the operative wound. The extension arm transfers a force applied to it, for example by a hammer, to the impaction member located within the operative wound such that the impaction member contacts the tibial implant and forces the keel into the slot in the tibial plateau. The extension arm may extend above the femur and have a portion which extends parallel with the impaction member.

Since the impaction member enters the operative wound it is essential that it is satisfactorily sterilised and free from germs in order to prevent infection of the wound. The present invention therefore seeks to provide a surgical impactor which may be easily sterilised.

STATEMENTS OF INVENTION

According to a first aspect of the present invention, there is provided a surgical impactor for inserting a prosthetic implant into a bone, the surgical impactor comprising: a movable retaining means for releasably connecting the implant to the surgical impactor, wherein the retaining means has a first position in which the implant is connected to the surgical impactor and a second position in which the implant is not connected to the surgical impactor; and a mechanism for moving the movable retaining means between the first and second positions, wherein the movable retaining means and the mechanism are removable from the surgical impactor.

The surgical impactor may further comprise a fixed retaining means which cooperates with the movable retaining means to connect the implant to the surgical impactor; wherein the implant may be received between the fixed retaining means and the movable retaining means.

The movable retaining means may comprise a foot and a threaded portion, the foot being attached to the threaded portion.

The mechanism may comprise a threaded wheel for receiving the threaded portion of the movable retaining means, wherein the threaded wheel may be rotatable about a position fixed relative to the surgical impactor, such that rotation of the threaded wheel causes translation of the foot.

The foot and the threaded wheel may be separated by a separating portion of the surgical impactor, wherein the threaded portion may pass through an opening in the separating portion.

The surgical impactor may further comprise a removable portion which allows removal of the movable retaining means and the mechanism.

In use, the threaded wheel may be disposed between the foot and the removable portion.

The removable portion may comprise a bore for receiving the threaded portion.

The surgical impactor may be a tibial impactor for inserting a tibial implant into a tibia.

According to a second aspect of the present invention, there is provided a method of disassembling a surgical impactor for sterilisation, the surgical impactor comprising: a movable retaining means having a foot and a threaded portion, the foot being attached to the threaded portion, and a mechanism for moving the movable retaining means, the mechanism having a threaded wheel for receiving the threaded portion of the movable retaining means, the surgical impactor further comprising a removable portion; the method comprising: removing the removable portion from the surgical impactor; unscrewing the threaded wheel from the threaded portion of the movable retaining means; and removing the movable retaining means from the surgical impactor.

The method may further comprise sterilising the disassembled surgical impactor.

BRIEF DESCRIPTION OF THE DRAWINGS

For a better understanding of the present invention, and to show more clearly how it may be carried into effect, reference will now be made, by way of example, to the accompanying drawings, in which.

DETAILED DESCRIPTION

Figure 1:
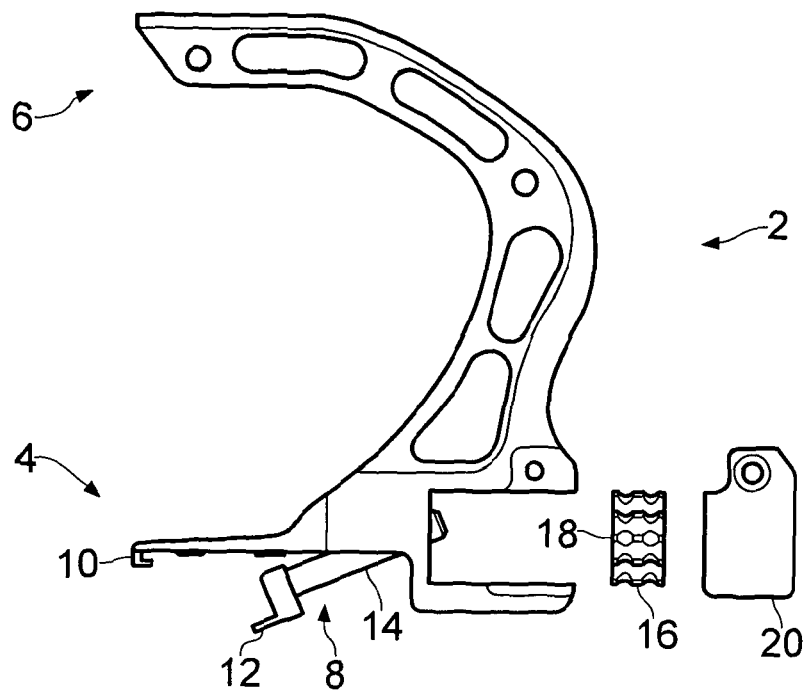
FIG. 1 is a side view of a disassembled surgical impactor in accordance with an aspect of the invention.

FIG. 1 shows a disassembled surgical impactor 2 in accordance with an embodiment of the invention. The surgical impactor comprises a impaction member 4 and an extension arm 6. The surgical impactor 2 further comprises a movable retaining means 8 and a fixed retaining means 10. The movable retaining means 8 consists of a foot 12 and a threaded portion 14. A threaded wheel 16 is provided having a threaded bore 18 extending therethrough for receiving the threaded portion 14 of the movable retaining means 8. The surgical impactor has a removable portion 20 which may be secured to the surgical impactor by screws or other fixation means which allow for its repeated removal.

Figure 2:
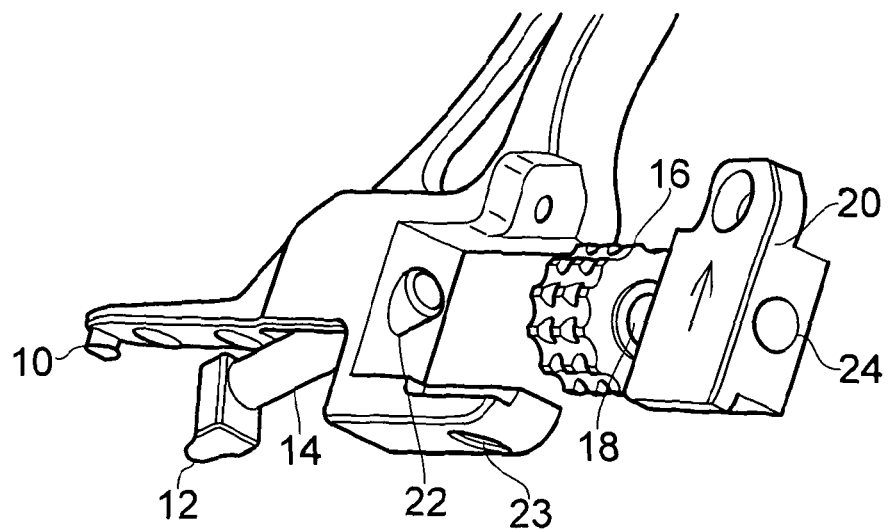
FIG. 2 is an enlarged perspective view of the disassembled surgical impactor.

As shown in FIG. 2, the threaded portion 14 of the movable retaining means 8 passes through an opening 22 in a separating portion of the surgical impactor 2. The opening 22 is sized to allow the threaded portion to be angled and then translated and rotated to align it with the threaded bore 18 of the threaded wheel 16. However, the size of the opening 22 prevents the foot 12 from passing through it. The threaded wheel 16 is disposed between the foot 12 and the removable portion 20 and between the opening 22 and the removable portion 20. The removable portion 20 has a bore 24 extending therethrough for receiving the threaded portion.

Figure 3:
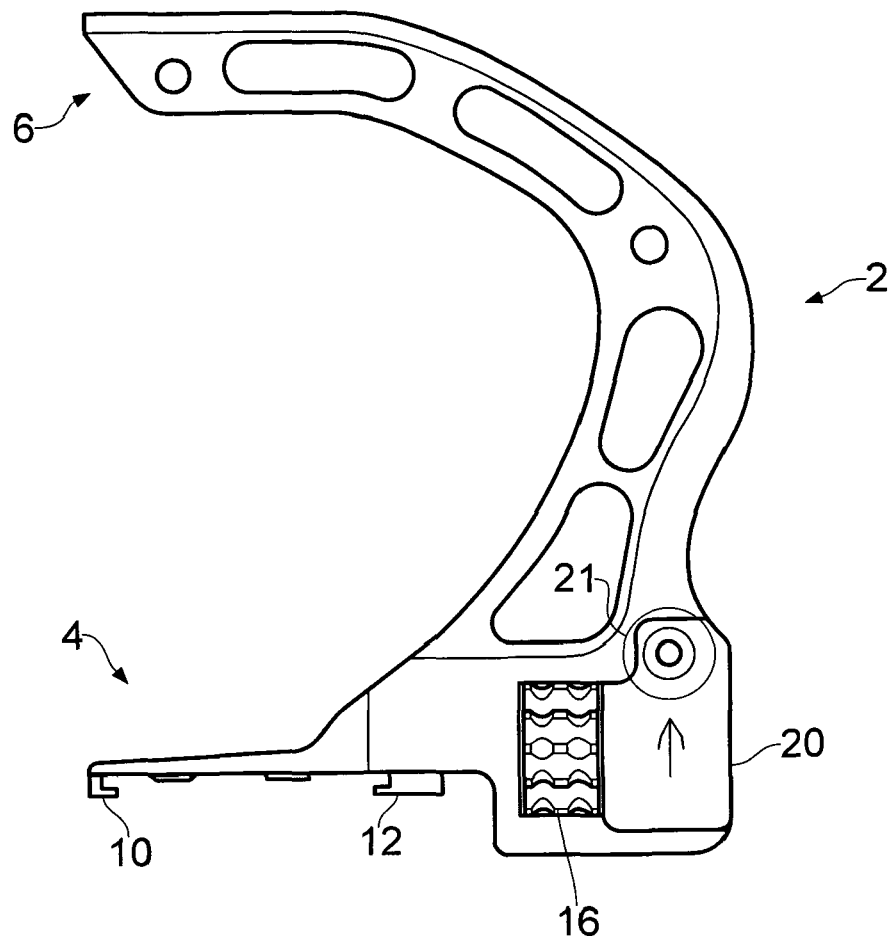
FIG. 3 is a side view of the surgical impactor following assembly.

When assembled, as shown in FIG. 3, the threaded portion 14 of the movable retaining means 8 passes through the opening 22 and into the threaded bore 18 of the threaded wheel 16. The threaded wheel 16 is rotatable about a position which is fixed relative to the surgical impactor by the removable portion 20. The removable portion 20 is secured to the surgical impactor by a first screw 21 and by a second screw (not shown). The second screw passes through the hole 23, as shown in FIG. 2, and into the removable portion 20.

Figure 4:
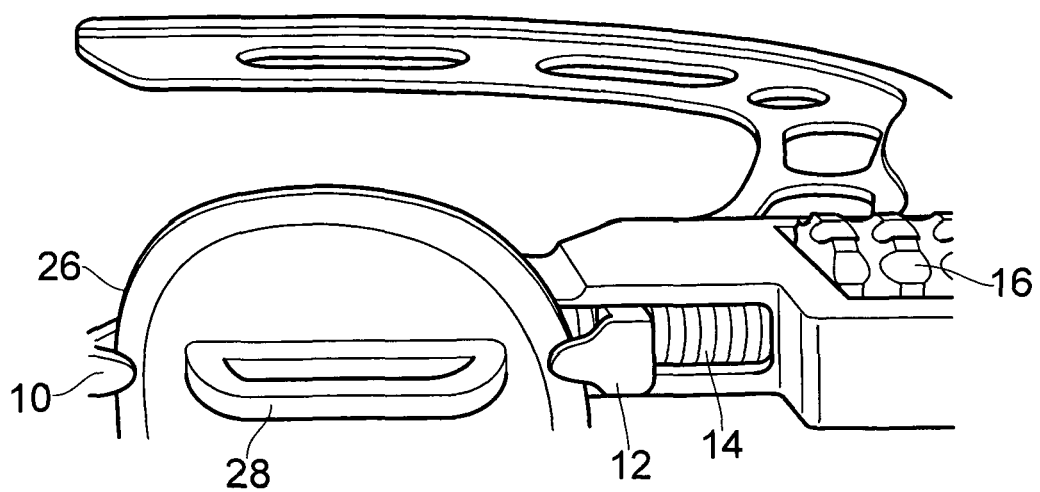
FIG. 4 is a bottom perspective view of the surgical impactor having a tibial component attached thereto.

In use, rotation of the threaded wheel 16 causes the threaded portion 14 to screw through the threaded bore 18. The section of the threaded portion 14 which is screwed through the threaded bore 18 passes into the bore 24 of the removable portion 20. Therefore, rotation of the threaded wheel 16 causes the movable retaining means 8 to translate toward or away from the fixed retaining means 10. As shown in FIG. 4, the movable retaining means 8 may be translated in order to retain a tibial component 26 between the foot 12 of the movable retaining means 8 and the fixed retaining means 10. The threaded wheel 16 is tightened to ensure the tibial component 26 is secured to the surgical impactor 2.

Figure 5:
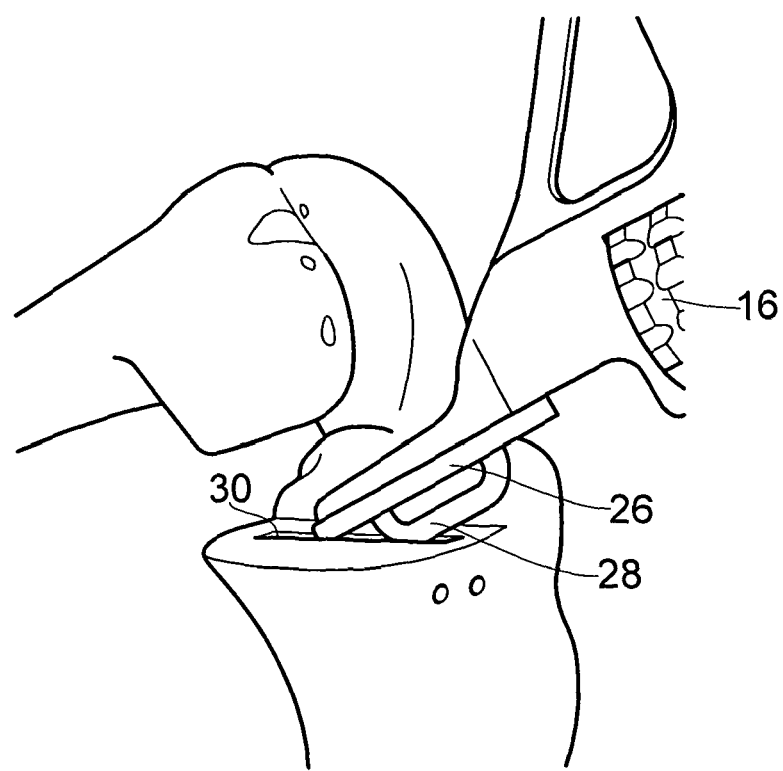
FIG. 5 is a perspective view of the surgical impactor in use.

The tibial component 26 has a keel 28 which extends from a bottom surface of the tibial component 26. As shown in FIG. 5, the surgical impactor 2 with the tibial component 26 attached is then passed through the operative wound to locate the keel 28 of the tibial component 26 in a slot 30 cut in the tibial plateau of the patient. The slot 30 and the keel 28 have an interference fit. Once the keel 28 is correctly located in the slot 30, the extension arm 6 is impacted to force the keel 28 into the slot 30. The threaded wheel 16 is undone so as to disconnect the tibial component 26 from the surgical impactor 2 before the tibial component is fully seated. The tibial component 26 is then further impacted to fully seat the tibial component 26 flush against the tibial plateau of the patient.

The design of the surgical impactor 2 is such that all movable parts can be removed to allow thorough sterilisation of the surgical impactor 2. In order to disassemble the surgical impactor 2, the removable portion 20 is first removed by undoing the first screw 21 and the second screw (not shown). The threaded wheel 16 may then be fully unscrewed from the threaded portion 14 of the movable retaining means 8 and removed from the surgical impactor 2. Finally, the movable retaining means 8 may be removed. Due to the size of the opening 22, the movable retaining means 8 must be removed in the opposite direction to the threaded wheel 16, as shown in FIG. 1. However this need not be the case, and the opening 22 could be of sufficient size to allow the foot 12 to pass through it so that the movable retaining means 8 may be removed in the same direction as the threaded wheel 16. This may allow the threaded wheel 16 and movable retaining means 8 to be removed whilst they are still connected.

The threaded wheel 16 and movable retaining means 8 may be later disconnected and sterilised.

As has been described, the present invention provides a surgical impactor having a movable retaining means for releasably connecting an implant to the surgical impactor, wherein the retaining means has a first position in which the implant is connected to the impactor and a second position in which the implant is not connected to the impactor; and a mechanism for moving the retaining means between the first and second positions, wherein the movable retaining means and the mechanism are removable from the surgical impactor. The present invention therefore provides an improved surgical impactor which can be more thoroughly sterilised in order to prevent infection in the operative wound.

The invention claimed is:

1. A surgical impactor for use in inserting a prosthetic implant into a bone, the surgical impactor comprising:
   a body having a monolithic construction and defining an extension arm having a curved shape, the body further defining a retaining arm, the retaining arm defining an indentation;
   a movable retaining member connected to a first end of a threaded shaft, the threaded shaft of the movable retaining member configured to pass through the body to cooperate the movable retaining member with the indentation of the retaining arm to releasably connect the prosthetic implant to the body between the indentation and the movable retaining member, wherein the movable retaining member has a first position in which the prosthetic implant is connected to the body and a second position in which the prosthetic implant is released from the body;
   a threaded wheel housed within a portion of the body, the threaded wheel defining a threaded hole through which a second end of the threaded shaft passes, the threaded wheel configured to move the movable retaining member between the first and second positions, towards and away from the retaining arm, upon rotation of the threaded wheel within the portion of the body in a first direction and a second direction, respectively, wherein the movable retaining member and the threaded wheel are removable from the body, and wherein the threaded wheel is rotatable about a position that is axially fixed relative to the portion of the body in which the threaded wheel is housed;
   a separate removable portion configured to be removably coupled and fixed in the portion of the body in which the threaded wheel is housed via a threaded fastener passing through the separate removable portion and into the portion of the body in which the threaded wheel is housed, wherein the threaded wheel is disposed between the movable retaining member and the separate removable portion when removably fixed in the portion of the body; and wherein the second end of the threaded shaft passes through the portion of the body in which the threaded wheel is housed, through the threaded wheel, and through an opening in the separate removable portion when the threaded wheel is housed within the portion of the body and the separate removable portion is coupled and fixed in the portion of the body.

2. The surgical impactor as claimed in claim 1, wherein the movable retaining member defines a foot configured to receive the prosthetic implant.

3. The surgical impactor as claimed in claim 2, wherein rotation of the threaded wheel causes translation of the foot.

4. The surgical impactor as claimed in claim 3, wherein the foot and the threaded wheel are separated by a separating portion of the body.

5. The surgical impactor as claimed in claim 1, wherein removal of the removable portion allows removal of the movable retaining member and the threaded wheel from the body.

6. The surgical impactor as claimed in claim 1, wherein the surgical impactor is a tibial impactor for inserting a tibial implant into a tibia.

7. A surgical impactor for use in inserting a prosthetic implant into a bone, the surgical impactor comprising:
a monolithic body defining a curved extension arm and defining an impaction member extending from the extension arm, the impaction member having a fixed retaining member having a hook shape; and
a movable retaining member connected to a threaded shaft, wherein the threaded shaft of the movable retaining member is configured to pass through the body to move the movable retaining member between a first position relative to the fixed retaining member where the prosthetic implant is held by the body and a second position relative to the fixed retaining member where the prosthetic implant is released by the body;
a threaded wheel defining a threaded hole through which the threaded shaft passes, the threaded wheel is housed within a portion of the body, the threaded wheel configured to move the movable retaining member between the first and second positions, towards and away from the fixed retaining member, upon rotation of the threaded wheel within the portion of the body in a first direction and a second direction, respectively, wherein the threaded wheel is rotatable about an axially fixed position within the portion of the body in which the threaded wheel is housed, and wherein the movable retaining member and the threaded wheel are removable from the body;
a separate removable portion removably coupled and fixed in the portion of the body in which the threaded wheel is housed via a fastener passing through the separate removable portion and the portion of the body in which the threaded wheel is housed, wherein the threaded wheel is disposed between the movable retaining member and the separate removable portion when removably fixed in the portion of the body in which the threaded wheel is housed; and the threaded shaft passing through the threaded hole defined by the threaded wheel, through the portion of the body in which the threaded wheel is housed, and through an opening in the separate removable portion when the threaded wheel is housed within the portion of the body and the separate removable portion is coupled and fixed in the portion of the body.

8. The surgical impactor as claimed in claim 7, wherein the extension arm has a C-shaped profile.

9. The surgical impactor as claimed in claim 7, wherein the movable retaining member includes a foot configured to engage the prosthetic implant and the threaded shaft, the threaded shaft extending from the foot, and through a bored formed in the body.

10. A surgical impactor for use in inserting a prosthetic implant into a bone, the surgical impactor comprising:
a monolithic body defining a curved extension arm and defining a fixed retaining member having a foot sized to accept the prosthetic implant;
a movable retaining member coupled to a threaded shaft, the movable retaining member having a foot sized to accept the prosthetic implant, wherein the threaded shaft of the movable retaining member is configured to pass through the body to move the movable retaining member from a first position to a second position relative to the fixed retaining member to retain and release, respectively, the prosthetic implant to and from the body;
a rotatable wheel defining a threaded bore through which the threaded shaft passes, the threaded wheel is housed within a portion of the body, the rotatable wheel configured to move the movable retaining member between the first and second positions, towards and away from the fixed retaining member, upon rotation of the threaded wheel within the portion of the body in a first direction and a second direction, respectively, wherein the rotatable wheel is rotatable about an axially fixed position within the portion of the body in which the rotatable wheel is housed, and wherein the movable retaining member and the threaded wheel are removable from the body;
a separate removable portion removably coupled and fixed in the portion of the body in which the rotatable wheel is housed, wherein the rotatable wheel is disposed between the movable retaining member and the separate removable portion when the separate removable portion is removably fixed in the portion of the body in which the rotatable wheel is housed; and
the threaded shaft passing through the threaded bore defined by the rotatable wheel, through the portion of the body in which the rotatable wheel is housed, and through a through bore in the separate removable portion when the threaded wheel is housed within the portion of the body and the separate removable portion is coupled and fixed in the portion of the body.

11. The surgical impactor as claimed in claim 10, wherein the extension arm has a C-shaped profile.

* * * * *